US008569224B2

(12) United States Patent
Köhle et al.

(10) Patent No.: US 8,569,224 B2
(45) Date of Patent: Oct. 29, 2013

(54) FABRIC SOFTENER ACTIVE COMPOSITION

(75) Inventors: Hans-Jürgen Köhle, Mainhausen (DE); Ulrike Kottke, Grossenhausen-Linsengericht (DE); Harald Jakob, Hasselroth (DE); Jens Hildebrand, Midlothian, VA (US)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/072,701

(22) Filed: Mar. 26, 2011

(65) Prior Publication Data

US 2011/0245138 A1    Oct. 6, 2011

Related U.S. Application Data

(60) Provisional application No. 61/319,950, filed on Apr. 1, 2010.

(51) Int. Cl.
*C11D 3/60* (2006.01)

(52) U.S. Cl.
USPC ........................................................ 510/515

(58) Field of Classification Search
USPC ........................................................ 510/515
See application file for complete search history.

(56) References Cited

U.S. PATENT DOCUMENTS

| | | | |
|---|---|---|---|
| 4,234,627 A | 11/1980 | Schilling | |
| 4,514,461 A | 4/1985 | Woo | |
| 4,747,880 A | 5/1988 | Berrido | |
| RE32,713 E | 7/1988 | Woo | |
| 4,789,491 A * | 12/1988 | Chang et al. | 510/525 |
| 4,882,220 A | 11/1989 | Ono et al. | |
| 4,917,920 A | 4/1990 | Ono et al. | |
| 5,137,646 A | 8/1992 | Schmidt et al. | |
| 5,391,325 A | 2/1995 | Swenson | |
| 5,480,567 A | 1/1996 | Lam et al. | |
| 5,703,029 A | 12/1997 | Crass | |
| 5,759,990 A | 6/1998 | Wahl et al. | |
| 5,792,219 A | 8/1998 | Hartman et al. | |
| 5,827,451 A | 10/1998 | Cummings | |
| 6,180,593 B1 | 1/2001 | Fender et al. | |
| 6,200,949 B1 | 3/2001 | Reijimer et al. | |
| 6,235,914 B1 | 5/2001 | Steiger | |
| 6,255,274 B1 | 7/2001 | Becherer | |
| 6,376,455 B1 * | 4/2002 | Friedli et al. | 510/515 |
| 6,458,343 B1 * | 10/2002 | Zeman et al. | 424/63 |
| 6,492,322 B1 | 12/2002 | Cooper et al. | |
| 6,608,024 B1 * | 8/2003 | DuVal et al. | 510/522 |
| 6,645,479 B1 | 11/2003 | Shefer et al. | |
| 6,653,275 B1 * | 11/2003 | Fender et al. | 510/527 |
| 6,770,608 B2 | 8/2004 | Franklin et al. | |
| 6,897,194 B2 | 5/2005 | Fan et al. | |
| 6,987,074 B2 | 1/2006 | Ishii | |
| 7,572,761 B2 | 8/2009 | Gefvert | |
| 7,704,940 B2 | 4/2010 | Boerefijn et al. | |
| 7,994,110 B2 | 8/2011 | Wenk et al. | |
| 8,183,199 B2 | 5/2012 | Fossum et al. | |
| 2003/0060390 A1 | 3/2003 | Demeyere et al. | |
| 2003/0158344 A1 | 8/2003 | Rodrigues et al. | |
| 2003/0165692 A1 | 9/2003 | Koch et al. | |
| 2003/0195130 A1 | 10/2003 | Lentsch et al. | |
| 2003/0195133 A1 | 10/2003 | Shefer et al. | |
| 2003/0203829 A1 | 10/2003 | Shefer et al. | |
| 2003/0215417 A1 | 11/2003 | Uchiyama et al. | |
| 2003/0216282 A1 | 11/2003 | Martens et al. | |
| 2003/0216488 A1 | 11/2003 | Uchiyama et al. | |
| 2003/0220210 A1 | 11/2003 | DuVal et al. | |
| 2004/0071742 A1 | 4/2004 | Popplewell et al. | |
| 2004/0071746 A1 | 4/2004 | Popplewell et al. | |
| 2004/0072719 A1 | 4/2004 | Bennett et al. | |
| 2004/0072720 A1 | 4/2004 | Brain et al. | |
| 2004/0087477 A1 | 5/2004 | Ness | |
| 2004/0106536 A1 | 6/2004 | Mane et al. | |
| 2004/0167056 A1 | 8/2004 | Lentsch et al. | |
| 2004/0204337 A1 | 10/2004 | Corona et al. | |
| 2005/0014672 A1 | 1/2005 | Arif | |
| 2005/0032671 A1 | 2/2005 | Kvita et al. | |
| 2006/0089293 A1 * | 4/2006 | Frankenbach | 510/515 |

(Continued)

FOREIGN PATENT DOCUMENTS

| | | |
|---|---|---|
| CA | 1312619 | 1/1993 |
| CS | 246532 | 3/1986 |

(Continued)

OTHER PUBLICATIONS

Price-Jones, et al., "*N,N*'-ethylenediyl-*bis*-alkanamides: Differential scanning calorimetry studies," *J. Am. Oil Chem. Soc.* 73:311-319 (1996).
Product Advertisement for Tetranyl AO-1, http//kaochemicals-eu.com/213.html, downloaded Jul. 27, 2011.
U.S. Appl. No. 13/168,958, filed Jun. 25, 2011, Schick.
International Search Report for PCT/EP2011/054107 filed Mar. 18, 2011.
Written Opinion of the International Searching Authority for PCT/EP2011/054107 filed Mar. 18, 2011.
International Search Report for PCT/EP2011/054282 filed Mar. 22, 2011, which is the international counterpart of copending U.S. Appl. No. 13/072,703.
Written Opinion of the International Searching Authority for PCT/EP2011/054282 filed Mar. 22, 2011.

(Continued)

*Primary Examiner* — Mark Eashoo
*Assistant Examiner* — M. Reza Asdjodi
(74) *Attorney, Agent, or Firm* — Law Office of: Michael A. Sanzo

(57) ABSTRACT

A fabric softener active composition, comprising at least 50% by weight of a bis-(2-hydroxypropyl)-dimethylammonium methylsulphate fatty acid ester having a molar ratio of fatty acid moieties to amine moieties of from 1.5 to 1.99, wherein the average chain length of the fatty acid moieties is from 16 to 18 carbon atoms and the iodine value of the fatty acid moieties, calculated for the free fatty acid, is from 0.5 to 50, and from 0.5 to 5% by weight fatty acid provides high softening performance and good storage stability in aqueous dispersion and can be handled and processed in a liquid state without addition of a flammable solvent.

20 Claims, No Drawings

(56) References Cited

U.S. PATENT DOCUMENTS

| | | |
|---|---|---|
| 2006/0094639 A1 | 5/2006 | Martin et al. |
| 2006/0142175 A1 | 6/2006 | Haiss et al. |
| 2006/0277689 A1 | 12/2006 | Hubig et al. |
| 2007/0054835 A1* | 3/2007 | Corona et al. ............... 510/515 |
| 2007/0066510 A1 | 3/2007 | Tee et al. |
| 2007/0219111 A1 | 9/2007 | Ward et al. |
| 2008/0242584 A1* | 10/2008 | Wahl et al. .................. 510/517 |
| 2008/0263780 A1* | 10/2008 | Declercq et al. ................ 8/137 |
| 2008/0289116 A1 | 11/2008 | Young et al. |
| 2009/0124533 A1 | 5/2009 | Kottke et al. |
| 2009/0181877 A1 | 7/2009 | McGinnis et al. |
| 2009/0203571 A1* | 8/2009 | Nagy et al. ................... 510/525 |
| 2011/0110993 A1 | 5/2011 | Chieffi et al. |
| 2011/0239377 A1 | 10/2011 | Fossum et al. |
| 2011/0239378 A1 | 10/2011 | Fossum et al. |
| 2011/0245139 A1 | 10/2011 | Köhle et al. |
| 2011/0245140 A1 | 10/2011 | Demeyere |
| 2012/0088712 A1 | 4/2012 | Schick et al. |

FOREIGN PATENT DOCUMENTS

| | | |
|---|---|---|
| DE | 24 30 140 A1 | 2/1976 |
| DE | 34 02 146 A1 | 7/1985 |
| DE | 36 08 093 A1 | 9/1987 |
| DE | 197 08 133 | 12/1997 |
| EP | 0 284 036 | 9/1988 |
| EP | 0 293 955 A2 | 12/1988 |
| EP | 0 302 567 A2 | 2/1989 |
| EP | 0 421 146 A2 | 9/1990 |
| EP | 0 829 531 A1 | 3/1998 |
| EP | 1 018 541 A1 | 7/2000 |
| EP | 1 323 817 A1 | 12/2001 |
| EP | 1 393 706 A1 | 3/2004 |
| EP | 1 840 197 A1 | 2/2007 |
| GB | 2 007 734 A | 5/1979 |
| GB | 2 039 556 | 8/1980 |
| WO | WO 91/01295 | 2/1991 |
| WO | WO 92/18593 | 10/1992 |
| WO | WO 94/14935 | 7/1994 |
| WO | WO 94/19439 | 9/1994 |
| WO | WO 98/38277 | 9/1998 |
| WO | WO 00/06678 | 2/2000 |
| WO | WO 2005/085404 A1 | 9/2005 |
| WO | WO 2007/026314 A2 | 3/2007 |
| WO | WO 2007/125005 | 11/2007 |
| WO | WO 2008/104509 | 9/2008 |
| WO | WO 2009/018955 A2 | 2/2009 |
| WO | WO 2011/120836 A1 | 10/2011 |
| WO | WO 2011/123284 A1 | 10/2011 |
| WO | WO 2011/123606 A1 | 10/2011 |
| WO | WO 2011/123733 A1 | 10/2011 |

OTHER PUBLICATIONS

English language abstract for EP 0 421 146 A2, listed as reference B1 above.
English language abstract for EP 1 323 817 A1, listed as reference B2 above.
English language abstract for DE 24 30 140, listed as document B1 above.
English language abstract for DE 36 08 093, listed as document B2 above.
English language abstract for EP 1 018 541, listed as document B5 above.
U.S. Appl. No. 13/072,703, filed Mar. 26, 2011, Köhle.
English language abstract for DE 34 02 146 A1, listed as reference B1 above.
English language abstract for WO2009/018955 A2, listed as reference B5 above.
Second English language abstract for WO2009/018955 A2, listed as reference B5 above.
English language translation of CS 246532, listed as document B2 above.
English language abstract for DE 197 08 133, listed as document B3 above.
English language abstract for EP 0 284 036, listed as document B4 above.
English language abstract for WO 91/01295, listed as document B6 above.
English language abstract for WO 94/14935, listed as document B8 above.
English language abstract for WO 2007/125005, listed as document B9 above.
Preliminary Amendment filed for copending U.S. Appl. No. 13/643,486 on Oct. 25, 2012.
U.S. Appl. No. 13/603,000, filed Sep. 4, 2012, Nagy.
U.S. Appl. No. 13/643,486, filed Oct. 25, 2012, Köhle.
Office Action mailed Jul. 31, 2012 in the prosecution of copending U.S. Appl. No. 13/072,703.
Response filed Oct. 9, 2012 in the prosecution of copending U.S. Appl. No. 13/072,703.
Ullman's Encyclopedia of Industrial Chemistry; Wiley-VCH Verlag GmbH & Co. KGaA, Weinheim, vol. 14, Table 2, p. 77 (2012).

* cited by examiner

FABRIC SOFTENER ACTIVE COMPOSITION

CROSS REFERENCE TO RELATED APPLICATIONS

The present application claims the benefit of U.S. provisional application 61/319,950 filed on Apr. 1, 2010

FIELD OF THE INVENTION

The present invention relates to fabric softener active compositions having high softening performance and good storage stability in aqueous formulations, which can be processed to aqueous formulations without the use of volatile solvents.

BACKGROUND OF THE INVENTION

Quaternary ammonium salts carrying two hydrophobic long chain hydrocarbon moieties have found broad use as fabric softener actives. Quaternary ammonium salts of alkanolamines esterified with on average two fatty acid moieties per molecule, commonly referred to as ester quats, have largely replaced earlier alkyl quaternary ammonium compounds because of their biodegradability.

For use in rinse cycle softener products, a softener active composition has to meet several and sometimes conflicting requirements:
  High softening performance in terms of soft touch and fabric rewettability,
  good storage stability in aqueous dispersion with little change in dispersion viscosity, and
  convenient handling and processing in a liquid state.

The ester quats which have found the broadest technical use and which today set the standard for softening performance are methyltriethanolammonium methylsulphate fatty acid diesters and dimethyldiethanolammonium chloride fatty acid diesters. However, aqueous dispersions of these fabric softener actives have limited stability and extended storage of such aqueous dispersions at temperatures in excess of 40° C. will usually lead to an unacceptable rise in dispersion viscosity or to settling of the softener active. Furthermore, these fabric softener actives cannot be handled and processed to aqueous dispersions without the addition of a solvent because of their high melting points and melt viscosities and the limited thermal and hydrolytic stability of the fabric softener actives. Therefore, they are usually delivered and processed with a content of 5 to 15% by weight ethanol or isopropanol, which requires additional precautions due to the volatility and flammability of the solvent.

EP 0 293 955 A2 and EP 0 302 567 A2 disclose aqueous fabric softener dispersions having high storage stability and little change in viscosity during storage and a method for preparing such dispersions. These compositions contain a bis-(2-hydroxypropyl)-dialkylammonium salt fatty acid diester as the fabric softener active in the form of submicrometer particles. However, preparation of these dispersions requires processing the fabric softener active mixed with from 5 to 50% by weight of a $C_1$-$C_4$ monohydric alcohol. In the examples, bis-(2-hydroxypropyl)-dimethylammonium chloride palmitic acid diester is used as the fabric softener active and isopropanol is used as the solvent.

DE 24 30 140 C3 discloses bis-(2-hydroxypropyl)-dialkylammonium salt fatty acid diesters for providing liquid fabric softener actives. Example 2 discloses the preparation of a bis-(2-hydroxypropyl)-dimethylammonium methylsulphate fatty acid diester by reacting a bis-(2-hydroxypropyl)-methylamine fatty acid diester of a fatty acid having an average chain length of 19 to 20 carbon atoms and comprising 90% by weight unsaturated fatty acid moieties with dimethyl sulphate in a molar ratio of 1:1.

EP 1 018 541 A1 discloses clear fabric softener compositions comprising an ester quat and an alkoxylated phenol or branched $C_3$-$C_6$ alcohol solvent. Example 6 discloses a composition containing a bis-(2-hydroxypropyl)-dimethylammonium methylsulphate fatty acid ester having a molar ratio of fatty acid moieties to amine moieties of 1.8 derived from a fatty acid having an average chain length of 18 carbon atoms and an iodine value of about 150. The ester quat active is processed with addition of 10% by weight isopropanol when making this composition, as disclosed in paragraph [0026].

WO 00/06678 discloses incompletely esterified ester quats of branched chain alkanolamines, which are claimed to have low melting points and high hydrolytic stability, and proposes to leave on average one hydroxyl group of the alkanolamine non-esterified. Example 50 discloses a bis-(2-hydroxypropyl)-dimethylammonium methylsulphate fatty acid ester made by quaternising a bis-(2-hydroxypropyl)-methylamine fatty acid ester having a molar ratio of fatty acid moieties to amine moieties of 1.26 derived from a fatty acid having a chain length of 12 to 14 carbon atoms.

DE 36 08 093 A1 discloses concentrated aqueous fabric softener compositions comprising an ester quat with two acyl groups, a fatty acid or an alkali salt thereof in an amount of 1/10 to 1/3 of the amount of the ester quat and a solvent combination of water, glycerol and an additional organic solvent in a total amount of 1/6 to twice the amount of the ester quat. Example 4 discloses a composition containing 45% by weight bis-(2-hydroxypropyl)-dimethylammonium methylsulphate oleic acid diester, 1% by weight tallow fatty acid sodium salt, 11.5% by weight water, 11.5% by weight glycerol, 17.5% by weight 2-propanol, 6% by weight propylene glycol and 3% by weight dipropylene glycol.

The ester quat actives disclosed in DE 24 30 140 C3, EP 1 018 541 A1 and WO 00/06678 have low melting points, but provide insufficient softening performance due to the high degree of unsaturation of the fatty acid moieties or the high content of monoester quat component. On the other hand, similar ester quats derived from bis-(2-hydroxypropyl)-methylamine with a low content of monoester quat, made from fatty acids with a low degree of unsaturation, as the one disclosed in EP 302 567 A2, provide the required softening performance, but show high melting points and melt viscosities and therefore require addition of a solvent for handling and processing.

Therefore, there is still a need for fabric softener actives which can be handled and processed without a solvent and without compromising storage stability in aqueous dispersion with little change in dispersion viscosity.

DESCRIPTION OF THE INVENTION

It has now been found that fabric softener active compositions based on a bis-(2-hydroxypropyl)-dimethylammonium methylsulphate fatty acid ester made from fatty acids with a specific chain length and a specific degree of unsaturation and having a particular molar ratio of fatty acid moieties to amine moieties, which comprise a specific amount of free fatty acid, provide high softening performance and good storage stability in aqueous dispersion, and at the same time can be handled and processed in a liquid state without addition of a flammable solvent.

The present invention is therefore directed to a fabric softener active composition, comprising at least 50% by weight of a bis-(2-hydroxypropyl)-dimethylammonium methylsulphate fatty acid ester having a molar ratio of fatty acid moieties to amine moieties of from 1.5 to 1.99, an average chain length of the fatty acid moieties of from 16 to 18 carbon atoms and an iodine value of the fatty acid moieties, calculated for the free fatty acid, of from 0.5 to 50, and from 0.5 to 5% by weight fatty acid.

The invention is also directed to a method for making such compositions, comprising the steps of reacting bis-(2-hydroxypropyl)-methylamine with a fatty acid having an average chain length of from 16 to 18 carbon atoms and an iodine value of from 0.5 to 50 in a molar ratio of fatty acid to amine of from 1.51 to 2.1 with removal of water until the acid value of the reaction mixture is in the range from 1 to 10 mg KOH/g and further reacting with dimethyl sulphate at a molar ratio of dimethyl sulphate to amine of from 0.90 to 0.97 and preferably from 0.92 to 0.95 until the total amine value of the reaction mixture is in the range from 1 to 8 mg KOH/g.

The fabric softener active composition of the invention comprises at least 50% by weight of a bis-(2-hydroxypropyl)-dimethylammonium methylsulphate fatty acid ester. The composition preferably comprises from 85 to 99% by weight of said ester. The use of a methylsulphate salt surprisingly provides both a lower melting point of the composition and a better stability to hydrolysis of an aqueous dispersion of the composition compared to a chloride salt as used in EP 0 293 955 A2 and EP 0 302 567 A2.

The bis-(2-hydroxypropyl)-dimethylammonium methylsulphate fatty acid ester is a mixture of at least one diester of formula $(CH_3)_2N^+(CH_2CH(CH_3)OC(=O)R)_2 CH_3OSO_3^-$ and at least one monoester of formula $(CH_3)_2N^+(CH_2CH(CH_3)OH)(CH_2CH(CH_3)OC(=O)R) CH_3OSO_3^-$, where R is the hydrocarbon group of a fatty acid moiety RCOO. The bis-(2-hydroxypropyl)-dimethylammonium methylsulphate fatty acid ester has a molar ratio of fatty acid moieties to amine moieties of from 1.5 to 1.99 and preferably from 1.85 to 1.99. The specified molar ratio is essential for simultaneously achieving high softening performance and low melting point of the composition. A molar ratio in the range from 1.85 to 1.99 provides high softening performance in the absence of anionic surfactants or at low concentrations of such surfactants. Fabric softener active compositions having such a molar ratio are therefore useful for making rinse cycle softeners intended for use in a laundry washing application where the laundry is rinsed several times after the wash before the rinse cycle softener is added. A molar ratio in the range from 1.5 to less than 1.85 provides good softening performance in the presence of anionic surfactants. Fabric softener active compositions having such a molar ratio are therefore useful for making rinse cycle softeners intended for use in a laundry washing application where the rinse cycle softener is added to the rinse immediately following the wash.

The fatty acid moiety of the bis-(2-hydroxypropyl)-dimethylammonium methylsulphate fatty acid ester is derived from a mixture of fatty acids of formula RCOOH, where R is a hydrocarbon group. The hydrocarbon group may be branched or unbranched and preferably is unbranched.

The fatty acid moiety has an average chain length of from 16 to 18 carbon atoms and an iodine value, calculated for the free fatty acid, of from 0.5 to 50. The average chain length is preferably from 16.5 to 17.8 carbon atoms. Preferably, the fatty acid moiety has an iodine value of from 1.0 to 50, more preferably of from 2 to 50, even more preferably of from 5 to 40 and most preferably of from 15 to 35. The average chain length is calculated on the basis of the weight fraction of individual fatty acids in the mixture of fatty acids. For branched chain fatty acids the chain length refers to the longest consecutive chain of carbon atoms. The iodine value is the amount of iodine in g consumed by the reaction of the double bonds of 100 g of fatty acid, determined by the method of ISO 3961. In order to provide the required average chain length and iodine value, the fatty acid moiety is derived from a mixture of fatty acids comprising both saturated and unsaturated fatty acids. The unsaturated fatty acids are preferably monounsaturated fatty acids. The bis-(2-hydroxypropyl)-dimethylammonium methylsulphate fatty acid ester preferably comprises less than 6% by weight of multiply unsaturated fatty acid moieties. Examples of suitable saturated fatty acids are palmitic acid and stearic acid. Examples of suitable monounsaturated fatty acids are oleic acid and elaidic acid.

The cis-trans-ratio of double bonds of unsaturated fatty acid moieties is preferably higher than 55:45 and more preferably higher than 65:35. The fraction of multiply unsaturated fatty acid moieties may be reduced by selective touch hydrogenation, which is a hydrogenation that selectively hydrogenates one double bond in a —CH=CH—CH$_2$—CH=CH— substructure but not double bonds of monounsaturated hydrocarbon groups. The specified average chain length and iodine values are essential for simultaneously achieving high softening performance and low melting point of the composition. If the average chain length is less than 16 carbon atoms or the iodine value is higher than 50, the softening performance will be unsatisfactory, whereas the melting point of the composition can get too high if the average chain length is more than 18 carbon atoms.

The fatty acid moiety may be derived from fatty acids of natural or synthetic origin and is preferably derived from fatty acids of natural origin, most preferably from fatty acids of plant origin. The required iodine value can be provided by using a fatty acid mixture of natural origin that already has such an iodine value, for example a tallow fatty acid. Alternatively, the required iodine value can be provided by partial hydrogenation of a fatty acid mixture or a triglyceride mixture having a higher iodine value. In a further and preferred embodiment, the required iodine value is provided by mixing a fatty acid mixture having a higher iodine value with a mixture of saturated fatty acids. The mixture of saturated fatty acids may be obtained either by hydrogenating a fatty acid mixture containing unsaturated fatty acids or from a hydrogenated triglyceride mixture, such as a hydrogenated vegetable oil.

The fabric softener active composition of the present invention further comprises from 0.5 to 5% by weight fatty acid in addition to the bis-(2-hydroxypropyl)-dimethylammonium methylsulphate fatty acid ester. The composition preferably comprises from 1 to 5% and more preferably from 2 to 5% by weight fatty acid. The fatty acid may be present as free fatty acid or in the form of a salt of the fatty acid with non-quaternised bis-(2-hydroxypropyl)-methylamine esters. The fabric softener active composition preferably comprises a fatty acid mixture, which is preferably of natural origin and most preferably of plant origin. In the most preferred embodiment, the fatty acid moieties of the bis-(2-hydroxypropyl)-dimethylammonium methylsulphate fatty acid ester are derived from the same fatty acid mixture as present in the composition in an amount of from 0.5 to 5% by weight. The specified amount of fatty acid is essential for achieving a low melting point of the composition without compromising storage stability in aqueous dispersion. If the composition comprises less than 0.5% by weight fatty acid, the melting point of the composition can get too high, whereas a content of more than 5% by weight fatty acid in the composition will have the effect that aqueous dispersions prepared from the composition have unsuitably high viscosities and low dispersion stability. By adjusting the amount of fatty acid within the claimed range, compositions of the present invention can be made which have low melt viscosities without using any solvent or diluent. Such compositions enable the manufacture of aqueous rinse cycle softener dispersions containing no solvent or a minimum amount of solvent.

The fabric softener active composition of the present invention preferably comprises less than 2% by weight and, more preferably, less than 0.5% by weight of water. Compositions having such low water content show improved storage stability in the molten state and therefore can be stored and delivered as liquids without compromising product quality. Compositions comprising more water show a much higher melt viscosity and are therefore difficult to process into an aqueous dispersion.

The fabric softener active composition of the present invention preferably comprises less than 10% by weight and more preferably less than 1% by weight of solvents having a flash point of less than 20° C.

In a preferred embodiment, the fabric softener active composition of the present invention comprises up to 9.9% by weight and preferably up to 5% by weight of at least one solvent selected from glycerol, ethylene glycol, propylene glycol, dipropylene glycol and C1-C4 alkyl monoethers of ethylene glycol, propylene glycol and dipropylene glycol. Examples of suitable glycol C1-C4 alkyl monoethers are 2-methoxyethanol, 2-ethoxyethanol, 2-butoxyethanol, 1-methoxy-2-propanol, dipropylene glycol monomethyl ether and dipropylene glycol monobutyl ether. The compositions according to this embodiment have the advantages of low melt viscosity and a close to Newtonian melt rheology, i.e. the viscosity shows little change with shear strength.

In another preferred embodiment, the fabric softener active composition of the present invention comprises from 2 to 8% by weight of a fatty acid triglyceride having an average chain length of the fatty acid moieties of from 10 to 14 carbon atoms and an iodine value, calculated for the free fatty acid, of from 0 to 15. Compositions according to this embodiment also have the advantages of low melt viscosity and a close to Newtonian melt rheology, i.e. the viscosity shows little change with shear strength.

In a preferred alternative embodiment, the amount of solvents present in the fabric softener active composition is less than 5% by weight and more preferably less than 1% by weight. The compositions according to this embodiment can be further processed in a molten state to provide aqueous solvent free dispersions.

In addition to a bis-(2-hydroxypropyl)-dimethylammonium methylsulphate fatty acid ester, a fatty acid and optionally a solvent, the fabric softener active composition of the present invention may preferably further comprise from 1.5 to 9% by weight of a bis-(2-hydroxypropyl)-methylamine fatty acid ester containing the same fatty acid moieties as the bis-(2-hydroxypropyl)-dimethylammonium methylsulphate fatty acid ester. The bis-(2-hydroxypropyl)-methylamine fatty acid ester is preferably a mixture of at least one diester of formula $(CH_3)N(CH_2CH(CH_3)OC(=O)R)_2$ and at least one monoester of formula $(CH_3)N(CH_2CH(CH_3)OH)(CH_2CH(CH_3)OC(=O)R)$. At least part of the bis-(2-hydroxypropyl)-methylamine fatty acid ester will be present in the form of a salt with the fatty acid of the fabric softener active composition. Such salts are of structure $HN^+(CH_3)(CH_2CH(CH_3)OC(=O)R)_2 RCOO^-$ or $HN^+(CH_3)(CH_2CH(CH_3)OH)(CH_2CH(CH_3)OC(=O)R)RCOO^-$. The presence of the bis-(2-hydroxypropyl)-methylamine fatty acid ester in the specified amount further lowers the melting point of the composition, without compromising softening performance and storage stability in aqueous dispersion.

The fabric softener active composition of the present invention may also further comprise minor amounts of (2-hydroxypropyl)-(1-methyl-2-hydroxyethyl)-dimethylammonium methylsulphate fatty acid esters, bis-(1-methyl-2-hydroxyethyl)-dimethylammonium methylsulphate fatty acid esters, (2-hydroxypropyl)-(1-methyl-2-hydroxyethyl)-methylamine fatty acid esters and bis-(1-methyl-2-hydroxyethyl)-methylamine fatty acid esters.

The fabric softener active composition of the present invention can be prepared by mixing the bis-(2-hydroxypropyl)-dimethylammonium methylsulphate fatty acid ester, the fatty acid and the optional components, such as solvent or bis-(2-hydroxypropyl)-methylamine fatty acid ester.

Preferably, the fabric softener active composition of the present invention is prepared by the method of the invention, comprising the steps of reacting bis-(2-hydroxypropyl)-methylamine with a fatty acid having an average chain length of from 16 to 18 carbon atoms and an iodine value of from 0.5 to 50 in a molar ratio of fatty acid to amine of from 1.51 to 2.1 with removal of water until the acid value of the reaction mixture is in the range from 1 to 10 mg KOH/g and further reacting with dimethyl sulphate at a molar ratio of dimethyl sulphate to amine of from 0.90 to 0.97 and preferably from 0.92 to 0.95 until the total amine value of the reaction mixture is in the range from 1 to 8 mg KOH/g.

In the first step of the method of the invention, bis-(2-hydroxypropyl)-methylamine is reacted with the fatty acid in a molar ratio of fatty acid to amine of from 1.51 to 2.1, preferably from 1.86 to 2.1, with removal of water. The reaction is preferably carried out at a temperature of from 160 to 220° C. Water is preferably removed by distillation from the reaction mixture. During the course of the reaction, the pressure is preferably reduced from ambient pressure to a pressure in the range from 100 to 5 mbar to enhance the removal of water. The first step may be carried out in the presence of an acidic catalyst, which is preferably used in an amount of from 0.05 to 0.2% by weight. Suitable acidic catalysts are methanesulfonic acid, p-toluenesulfonic acid and hypophosphorous acid. The reaction is carried out until the acid value of the reaction mixture is in the range from 1 to 10 mg KOH/g. The acid value is determined by titration with a standardised alkaline solution according to ISO 660 and is calculated as mg KOH per g sample. The reaction can then be stopped by cooling to a temperature below 80° C. in order to avoid further reaction of the fatty acid and maintain unreacted fatty acid to achieve the required amount of fatty acid in the final product.

In the second step of the method of the invention, the reaction mixture obtained in the first step is reacted with dimethyl sulphate at a molar ratio of dimethyl sulphate to amine of from 0.90 to 0.97 and preferably from 0.92 to 0.95. The reaction is preferably carried out at a temperature of from 60 to 100° C. The reaction is carried out until the total amine value of the reaction mixture is in the range from 1 to 8 mg KOH/g. The total amine value is determined by non-aqueous titration with perchloric acid according to method Tf 2a-64 of the American Oil Chemists Society and is calculated as mg KOH per g sample.

The method of the invention has the advantage of providing a fabric softener active composition according to the invention without requiring any step in addition to the steps needed for manufacturing the bis-(2-hydroxypropyl)-dimethylammonium methylsulphate fatty acid ester. This advantage is achieved by the appropriate choice of the molar ratio of fatty acid to amine and by carrying out the reaction of fatty acid and amine to the specified range of the acid value, maintaining a fraction of unreacted fatty acid.

The invention is illustrated by the following examples, which are however not intended to limit the scope of the invention in any way.

EXAMPLES

General

Table 1 lists the sources, fatty acid chain length distributions and iodine values of fatty acids A to G that were used in the examples. Fatty acid chain length distributions were determined by GC after derivatisation of the fatty acid as methyl ester.

Fabric softener active compositions were prepared by the following general procedure, unless specified otherwise in the individual examples. The fatty acid was placed with 0.2% by weight of 50% by weight hypophosphorous acid in an electrically heated reactor equipped with a thermometer, a mechanical stirrer and a rectifying column and the bis-(2-hydroxypropyl)-methylamine was added with stirring. The resulting mixture was heated with stirring to 200° C. and was kept at this temperature for 4 h at ambient pressure, distilling off water through the rectifying column. The pressure was then reduced to 10 mbar and the mixture was further stirred at 200° C., water being removed with a vacuum pump, for the time specified in the individual example until the desired acid value of the reaction mixture was reached. The resulting mixture was then cooled to 75° C., dimethyl sulphate was added and the resulting mixture was stirred for 2 h at 70 to 90° C.

Contents of free amine, amine salt and fatty acid in the fabric softener active composition were determined by non-aqueous potentiometric titration with tetrabutylammonium hydroxide after addition of an excess of a solution of HCl in 2-propanol.

TABLE 1

Sources, fatty acid chain length distributions and iodine values of fatty acids

| | Fatty acid | | | | | | |
|---|---|---|---|---|---|---|---|
| | A | B | C | D | E | F | G |
| Source | talloil* | tallow, partially hydrogenated | rapeseed | vegetable blend | coconut, hydrogenated | vegetable blend, partially hydrogenated | vegetable blend, hydrogenated |
| C12(0) | | | | | 46.4 | | |
| C14(0) | | 2.1 | | 0.2 | 53.6 | 0.8 | 2.6 |
| C15(0) | | 0.4 | | | | | |
| C16(0) | 0.7 | 27.9 | 3.2 | 19.2 | | 45.3 | 46.4 |
| C16(1) | | 0.7 | | 0.5 | | | |
| C17(0) | 0.2 | 1.1 | | | | | |
| C18(0) | 1.8 | 48.1 | 1.0 | 21.2 | | 13.4 | 49.3 |
| C18(1) | 29.3 | 15.1 | 17.1 | 47.6 | | 37.2 | |
| C18(2) | 46.3 | 0.9 | 12.7 | 7.9 | | 1.9 | |
| C18(3) | 0.9 | | 7.3 | | | | |
| C20(0) | 0.2 | 0.9 | 0.7 | 0.3 | | 0.2 | 1.9 |
| C20(1) | 0.4 | | 7.9 | 0.2 | | | |
| C22(0) | | | 0.7 | | | | |
| C22(1) | | | 45.9 | | | | |
| C22(2) | | | 0.7 | | | | |
| C24(0) | | | 0.2 | | | | |
| C24(1) | | | 0.8 | | | | |
| Average chain length | 18.0 | 17.3 | 20.1 | 17.6 | 13.1 | 17.1 | 17.0 |
| Iodine value | 150 | 20 | 102 | 61 | 0.1 | 37 | 0.7 |

Cx(y) denotes a linear fatty acid with x carbon atoms and y double bonds.
*20% of fatty acids could not be saponified and analysed.

Fractions of monoester and diester in the bis-(2-hydroxypropyl)-dimethylammonium methylsulphate fatty acid ester were determined by HPLC (Waters Spherisorb® SCX column, methanol eluent with a formic acid triethylamine buffer, RI detection).

Melting points were determined by the capillary method as the upper temperature of the melting range using a heating rate of 1° C./min. Samples were conditioned by melting the composition, homogenizing the melt, shock solidifying the melt by pouring it onto a cold metal plate and cooling the shock solidified melt to −16° C. for at least 4 h before transferring it to a melting point capillary.

Melt viscosities were measured at 70° C. with a StressTech rheometer of REOLOGICA® instruments using 40 mm parallel plates, a plate distance of 0.5 mm and shear rates of 1, 10 and 100 s$^{-1}$.

Storage stability was determined for 10% by weight aqueous dispersions of the fabric softener active compositions that were stored for 6 weeks at 50° C. in closed glass bottles. Dispersions were prepared by first dispersing a melt of the fabric softener active composition heated to 5 to 10° C. above the melting point in a 0.05% by weight aqueous HCl solution preheated to 5° C. below the melting point of the composition using an IKA Super-Dispax-Reactor® SD 41 operated at 8000 min$^{-1}$. Thereafter, a 25% by weight aqueous solution of CaCl$_2$ was added with stirring to provide a CaCl$_2$ concentration of 0.025% by weight. Acid values of the dispersions were determined before and after storage by acid-base-titration with KOH or NaOH and are given as mg KOH/g dispersion. Viscosity of the dispersions before and after storage was determined at 20° C. with a Brookfield viscosimeter using spindle number 1 for viscosities up to 100 mPa*s and spindle number 2 for viscosities higher than 100 mPa*s.

The softening performance of a fabric softener active composition was determined in a tactile test performed by a panel of test persons on pieces of cotton towel treated with an aqueous dispersion of the composition. 80 cm by 50 cm pieces of terry cloth cotton towel were washed twice with a heavy duty powder detergent, rinsed twice with intermediate and final spinning and dried in air hanging on a line. Samples of the 10% by weight aqueous dispersions of the fabric softener active compositions prepared as described above were diluted with cold tap water to give 2 l of a rinse solution containing 0.025% by weight fabric softener active composition. The washed cotton towel pieces were immersed in this rinse solution for 10 min, spun and dried in air at ambient temperature hanging on a line. Thereafter, the treated cotton towel pieces were cut in 10 equal pieces of 16 cm by 25 cm, which were distributed to a panel of 9 test persons who rated the softness on a scale ranging from 0 for hard and a bad feel to 5 for soft and a good feel. The softness rating given in the examples is the sum of the nine individual ratings and can therefore range from 0 to 45. Differences in the softness rating of more than 4 are statistically significant, as determined from comparative repeat experiments.

Example 1

Comparative Example, Corresponds to Component A5 of EP 1 018 541 A1

644 g (2.25 mol) fatty acid A was esterified with 182.5 g (1.25 mol) bis-(2-hydroxypropyl)-methylamine at 190° C. with 8 h reaction at reduced pressure until the acid value of the reaction mixture was 0.6 mg KOH/g. The resulting mixture was reacted with 151 g (1.20 mol) dimethyl sulphate at 60° C. The resulting fabric softener active composition was a brownish viscous liquid, containing 0.015 mmol/g (0.5% by weight) fatty acid and 0.070 mmol/g non-quaternised amine (0.041 mmol/g free amine and 0.029 mmol/g protonated amine). HPLC analysis showed the bis-(2-hydroxypropyl)-dimethylammonium methylsulphate fatty acid ester to be comprised of 8.2% monoester and 91.8% diester (rel. area percentages).

The composition had a melt viscosity of 685 mPa*s at 1 $s^{-1}$, 488 mPa*s at 10 $s^{-1}$ and 431 mPa*s at 100 $s^{-1}$ shear rate.

The 10% aqueous dispersion had an acid value of 0.6 mg KOH/g and a viscosity of 34 mPa*s before storage and an acid value of 1.2 mg KOH/g and a viscosity of 265 mPa*s after storage for 6 weeks at 50° C.

The composition achieved a softness rating of 12.

Example 2

Example 1 was repeated using 954 g (3.49 mol) of fatty acid B, 283 g (1.94 mol) bis-(2-hydroxypropyl)-methylamine and 235 g (1.86 mol) dimethyl sulphate. The resulting fabric softener active composition was a white solid with a melting point of 42° C., containing 0.025 mmol/g (0.7% by weight) fatty acid and 0.059 mmol/g non-quaternised amine (0.033 mmol/g free amine and 0.026 mmol/g protonated amine). HPLC analysis showed the bis-(2-hydroxypropyl)-dimethylammonium methylsulphate fatty acid ester to be comprised of 8.8% monoester and 91.2% diester (rel. area percentages).

The composition had a melt viscosity of 47200 mPa*s at 1 $s^{-1}$ 9880 mPa*s at 10 $s^{-1}$ and 2960 mPa*s at 100 $s^{-1}$ shear rate.

The 10% aqueous dispersion had an acid value of 0.5 mg KOH/g and a viscosity of 18 mPa*s before storage and an acid value of 1.1 mg KOH/g and a viscosity of 18 mPa*s after storage for 6 weeks at 50° C.

The composition achieved a softness rating of 32.

Example 3

Comparative Example, Corresponds to Example 2 of DE 24 30 140 C3

744.5 g (2.38 mol) fatty acid C was esterified with 174.1 g (1.19 mol) bis-(2-hydroxypropyl)-methylamine with 15 h reaction at reduced pressure until the acid value of the reaction mixture was 1.5 mg KOH/g. The resulting mixture was reacted with 142.5 g (1.13 mol) dimethyl sulphate for 4 h. The resulting fabric softener active composition was a yellowish gel, containing 0.032 mmol/g (1.0% by weight) fatty acid and 0.113 mmol/g non-quaternised amine (0.042 mmol/g free amine and 0.071 mmol/g protonated amine). The amounts of monoester and diester in the bis-(2-hydroxypropyl)-dimethylammonium methylsulphate fatty acid ester could not be determined by HPLC analysis.

The composition had a melt viscosity of 561 mPa*s at 1 $s^{-1}$ 535 mPa*s at 10 $s^{-1}$ and 469 mPa*s at 100 $s^{-1}$ shear rate.

A 10% by weight aqueous dispersion prepared with 0.025% by weight $CaCl_2$ was very viscous. Therefore, the dispersion for the stability test was prepared with a fourfold amount of $CaCl_2$, i.e. 0.1% by weight $CaCl_2$. The dispersion had an acid value of 0.7 mg KOH/g and a viscosity of 160 mPa*s before storage and an acid value of 1.4 mg KOH/g and a viscosity of 270 mPa*s after storage for 6 weeks at 50° C.

The composition achieved a softness rating of 24.

Example 4

Example 3 was repeated using 948 g (3.47 mol) of fatty acid B, 253.4 g (1.735 mol) bis-(2-hydroxypropyl)-methylamine and 208 g (1.65 mol) dimethyl sulphate with 15 h reaction at reduced pressure until the acid value of the reaction mixture was 1.4 mg KOH/g. The resulting fabric softener active composition was a white solid with a melting point of 43° C., containing 0.032 mmol/g (0.9% by weight) fatty acid and 0.073 mmol/g non-quaternised amine (0.043 mmol/g free amine and 0.030 mmol/g protonated amine). HPLC analysis showed the bis-(2-hydroxypropyl)-dimethylammonium methylsulphate fatty acid ester to be comprised of 3.1% monoester and 96.9% diester (rel. area percentages).

The composition had a melt viscosity of 36200 mPa*s at 1 $s^{-1}$, 7440 mPa*s at 10 $s^{-1}$ and 2160 mPa*s at 100 $s^{-1}$ shear rate.

The 10% aqueous dispersion had an acid value of 0.6 mg KOH/g and a viscosity of 16 mPa*s before storage and an acid value of 1.3 mg KOH/g and a viscosity of 18 mPa*s after storage for 6 weeks at 50° C.

The composition achieved a softness rating of 31.

Examples 1 and 4 and comparative examples 2 and 3 clearly demonstrate that the fabric softener active compositions of the invention provide a significantly better softening performance in terms of soft touch and a better storage stability of a 10% aqueous dispersion compared to the fabric softener active compositions known from EP 1 018 541 A1 and DE 24 30 140 C3.

Example 5

2780 g (10.18 mol) fatty acid B was esterified with 783 g (5.36 mol) bis-(2-hydroxypropyl)-methylamine with 3 h reaction at reduced pressure until the acid value of the reaction mixture was 5.2 mg KOH/g. The resulting mixture was reacted with 642 g (5.10 mol) dimethyl sulphate. The resulting fabric softener active composition was a white solid with a melting point of 41° C., containing 0.075 mmol/g (2.2% by weight) fatty acid and 0.123 mmol/g non-quaternised amine (0.068 mmol/g free amine and 0.055 mmol/g protonated amine). HPLC analysis showed the bis-(2-hydroxypropyl)-dimethylammonium methylsulphate fatty acid ester to be comprised of 5.5% monoester and 94.5% diester (rel. area percentages).

The composition had a melt viscosity of 2360 mPa*s at 1 $s^{-1}$, 1090 mPa*s at 10 $s^{-1}$ and 619 mPa*s at 100 $s^{-1}$ shear rate.

The 10% aqueous dispersion had an acid value of 0.8 mg KOH/g and a viscosity of 28 mPa*s before storage and an acid value of 2.8 mg KOH/g and a viscosity of 12 mPa*s after storage for 6 weeks at 50° C.

The composition achieved a softness rating of 35.

Example 6

1365 g (5.0 mol) fatty acid B was esterified with 384.2 g (2.63 mol) bis-(2-hydroxypropyl)-methylamine with 14 h reaction at reduced pressure until the acid value of the reaction mixture was 1.3 mg KOH/g. The resulting mixture was reacted with 315 g (2.5 mol) dimethyl sulphate. The resulting fabric softener active composition was a white solid with a melting point of 43° C., containing 0.025 mmol/g (0.7% by weight) fatty acid and 0.113 mmol/g non-quaternised amine (0.081 mmol/g free amine and 0.032 mmol/g protonated amine). HPLC analysis showed the bis-(2-hydroxypropyl)-dimethylammonium methylsulphate fatty acid ester to be comprised of 5.7% monoester and 94.3% diester (rel. area percentages).

The composition had a melt viscosity of 16200 mPa*s at 1 $s^{-1}$, 4970 mPa*s at 10 $s^{-1}$ and 1530 mPa*s at 100 $s^{-1}$ shear rate.

The 10% aqueous dispersion had an acid value of 0.5 mg KOH/g and a viscosity of 19 mPa*s before storage and an acid value of 1.9 mg KOH/g and a viscosity of 13 mPa*s after storage for 6 weeks at 50° C.

The composition achieved a softness rating of 32.

Example 7

The esterification step of example 6 was repeated and 1021 g of the reaction mixture obtained was mixed with 45 g fatty acid B. The resulting mixture was reacted with 193 g (1.53 mol) dimethyl sulphate. The resulting fabric softener active composition was a white solid with a melting point of 41° C., containing 0.151 mmol/g (4.15% by weight) fatty acid and 0.162 mmol/g non-quaternised amine (0.070 mmol/g free amine and 0.092 mmol/g protonated amine). HPLC analysis showed the bis-(2-hydroxypropyl)-dimethylammonium methylsulphate fatty acid ester to be comprised of 5.7% monoester and 94.3% diester (rel. area percentages).

The composition had a melt viscosity of 842 mPa*s at 1 $s^{-1}$ 663 mPa*s at 10 $s^{-1}$ and 619 mPa*s at 100 $s^{-1}$ shear rate.

The 10% aqueous dispersion had an acid value of 1.3 mg KOH/g and a viscosity of 23 mPa*s before storage and an acid value of 3.9 mg KOH/g and a viscosity of 8 mPa*s after storage for 6 weeks at 50° C.

The composition achieved a softness rating of 31.

Examples 5 to 7 demonstrate that the presence of fatty acid in the fabric softener active compositions of the invention contributes to a low melt viscosity of the composition, provides a closer to Newtonian rheology of the melt and does not adversely affect the viscosity of an aqueous dispersion of the composition during storage.

Example 8

Comparative, Higher Iodine Value 970 g (3.5 mol) fatty acid D was esterified with 287 g (1.84 mol) bis-(2-hydroxypropyl)-methylamine with 3 h reaction at reduced pressure until the acid value of the reaction mixture was 5.6 mg KOH/g. The resulting mixture was reacted with 221 g (1.75 mol) dimethyl sulphate. The resulting fabric softener active composition was a yellow viscous liquid, containing 0.054 mmol/g (1.6% by weight) fatty acid and 0.129 mmol/g non-quaternised amine (0.068 mmol/g free amine and 0.061 mmol/g protonated amine). HPLC analysis showed the bis-(2-hydroxypropyl)-dimethylammonium methylsulphate fatty acid ester to be comprised of 6.6% monoester and 93.4% diester (rel. area percentages).

The composition had a melt viscosity of 581 mPa*s at 1 $s^{-1}$ 538 mPa*s at 10 $s^{-1}$ and 480 mPa*s at 100 $s^{-1}$ shear rate.

The 10% aqueous dispersion had an acid value of 0.9 mg KOH/g and a viscosity of 40 mPa*s before storage and an acid value of 2.6 mg KOH/g and a viscosity of 36 mPa*s after storage for 6 weeks at 50° C.

The composition achieved a softness rating of 23.

Example 8 demonstrates that a fabric softener active composition, which has fatty acid moieties of the quaternary ammonium salt with an iodine value higher than claimed, does not achieve a softening performance as high as that of the fabric softener active composition of the invention.

Example 9

Comparative, Shorter Average Chain Length 1125 g (5.25 mol) fatty acid E was esterified with 403 g (2.76 mol) bis-(2-hydroxypropyl)-methylamine with 2 h reaction at reduced pressure until the acid value of the reaction mixture was 4.1 mg KOH/g. The resulting mixture was reacted with 330 g (2.62 mol) dimethyl sulphate. The resulting fabric softener active composition was a white gel, containing 0.049 mmol/g (1.1% by weight) fatty acid and 0.122 mmol/g non-quaternised amine (0.079 mmol/g free amine and 0.043 mmol/g protonated amine). HPLC analysis showed the bis-(2-hydroxypropyl)-dimethylammonium methylsulphate fatty acid ester to be comprised of 3.2% monoester and 96.8% diester (rel. area percentages).

The composition had a melt viscosity of 552 mPa*s at 1 $s^{-1}$, 550 mPa*s at 10 $s^{-1}$ and 497 mPa*s at 100 $s^{-1}$ shear rate.

The 10% aqueous dispersion had an acid value of 0.8 mg KOH/g and a viscosity of 30 mPa*s before storage and an acid value of 2.5 mg KOH/g and a viscosity of 79 mPa*s after storage for 6 weeks at 50° C.

The composition achieved a softness rating of 16.

Example 9 demonstrates that a fabric softener active composition, which has fatty acid moieties of the quaternary ammonium salt with an average chain length lower than claimed, does not achieve a softening performance as high as that of the fabric softener active composition of the invention.

Example 10

1032 g (3.78 mol) fatty acid B was esterified with 313.3 g (2.16 mol) bis-(2-hydroxypropyl)-methylamine with 2 h reaction at reduced pressure until the acid value of the reaction mixture was 4.6 mg KOH/g. The resulting mixture was reacted with 258.8 g (2.05 mol) dimethyl sulphate. The resulting fabric softener active composition was a white solid with a melting point of 41° C., containing 0.047 mmol/g (1.3% by weight) fatty acid and 0.134 mmol/g non-quaternised amine (0.076 mmol/g free amine and 0.058 mmol/g protonated amine). HPLC analysis showed the bis-(2-hydroxypropyl)-dimethylammonium methylsulphate fatty acid ester to be comprised of 16.6% monoester and 83.4% diester (rel. area percentages).

The composition had a melt viscosity of 27100 mPa*s at 1 $s^{-1}$, 6040 mPa*s at 10 $s^{-1}$ and 1870 mPa*s at 100 $s^{-1}$ shear rate.

The 10% aqueous dispersion had an acid value of 0.9 mg KOH/g and a viscosity of 19 mPa*s before storage and an acid value of 2.5 mg KOH/g and a viscosity of 13 mPa*s after storage for 6 weeks at 50° C.

The composition achieved a softness rating of 27.

Example 10 demonstrates that a fabric softener active composition, which has a molar ratio of fatty acid moieties to amine moieties lower than claimed, does not achieve a softening performance as high as that of the fabric softener active composition of the invention.

Example 11

919 g (3.37 mol) fatty acid B was esterified with 245.7 g (1.68 mol) bis-(2-hydroxypropyl)-methylamine with 7 h reaction at reduced pressure until the acid value of the reaction mixture was 5.5 mg KOH/g. The resulting mixture was reacted with 201.3 g (1.60 mol) dimethyl sulphate. The resulting fabric softener active composition was a white solid with a melting point of 43° C., containing 0.076 mmol/g (2.2% by weight) fatty acid and 0.141 mmol/g non-quaternised amine (0.084 mmol/g free amine and 0.057 mmol/g protonated amine). HPLC analysis showed the bis-(2-hydroxypropyl)-dimethylammonium methylsulphate fatty acid ester to be comprised of 0.9% monoester and 99.1% diester (rel. area percentages).

The composition had a melt viscosity of 1510 mPa*s at 1 $s^{-1}$, 687 mPa*s at 10 $s^{-1}$ and 553 mPa*s at 100 $s^{-1}$ shear rate.

The 10% aqueous dispersion had an acid value of 0.9 mg KOH/g and a viscosity of 31 mPa*s before storage and an acid value of 3.3 mg KOH/g and a viscosity of 12 mPa*s after storage for 6 weeks at 50° C.

The composition achieved a softness rating of 31.

Example 12

4823 g (17.68 mol) fatty acid F was esterified with 1337.4 g (9.16 mol) bis-(2-hydroxypropyl)-methylamine with 5 h reaction at ambient pressure and 5 h reaction at reduced pressure until the acid value of the reaction mixture was 4.6 mg KOH/g. The resulting mixture was reacted with 1096.5 g (8.70 mol) dimethyl sulphate. The resulting fabric softener active composition was a white solid with a melting point of 38° C., containing 0.069 mmol/g (2.0% by weight) fatty acid and 0.130 mmol/g non-quaternised amine (0.071 mmol/g free amine and 0.059 mmol/g protonated amine). HPLC analysis showed the bis-(2-hydroxypropyl)-dimethylammonium methylsulphate fatty acid ester to be comprised of 5.9% monoester and 94.1% diester (rel. area percentages).

The composition had a melt viscosity of 592 mPa*s at 1 $s^{-1}$, 610 mPa*s at 10 $s^{-1}$ and 552 mPa*s at 100 $s^{-1}$ shear rate.

The composition achieved a softness rating of 38.

Example 13

4088 g (14.9 mol) fatty acid G was esterified with 1129.5 g (7.74 mol) bis-(2-hydroxypropyl)-methylamine with 4 h reaction at reduced pressure until the acid value of the reaction mixture was 3.7 mg KOH/g. The resulting mixture was reacted with 926.5 g (7.4 mol) dimethyl sulphate. The resulting fabric softener active composition was a white solid with a melting point of 52° C., containing 0.066 mmol/g (1.9% by weight) fatty acid and 0.128 mmol/g non-quaternised amine (0.073 mmol/g free amine and 0.055 mmol/g protonated amine). HPLC analysis showed the bis-(2-hydroxypropyl)-dimethylammonium methylsulphate fatty acid ester to be comprised of 6.8% monoester and 93.2% diester (rel. area percentages).

The composition had a melt viscosity of 34700 mPa*s at 1 $s^{-1}$, 8100 mPa*s at 10 $s^{-1}$ and 2630 mPa*s at 100 $s^{-1}$ shear rate.

The composition achieved a softness rating of 38.

Example 14

2520.4 g (9.23 mol) fatty acid B was esterified with 692.5 g (4.75 mol) bis-(2-hydroxypropyl)-methylamine with 5 h reaction at reduced pressure until the acid value of the reaction mixture was 6.1 mg KOH/g. The resulting mixture was reacted with 568.6 g (4.51 mol) dimethyl sulphate for 1 h. Then 180.8 g dipropylene glycol was added and the mixture was homogenized by stirring. The resulting fabric softener active composition was a white solid with a melting point of 40° C., containing 0.083 mmol/g (2.4% by weight) fatty acid and 0.119 mmol/g non-quaternised amine (0.048 mmol/g free amine and 0.071 mmol/g protonated amine). HPLC analysis showed the bis-(2-hydroxypropyl)-dimethylammonium methylsulphate fatty acid ester to be comprised of 6.8% monoester and 93.2% diester (rel. area percentages).

The composition had a melt viscosity of 368 mPa*s at 1 $s^{-1}$, 340 mPa*s at 10 $s^{-1}$ and 318 mPa*s at 100 $s^{-1}$ shear rate.

Example 15

3214 g (11.77 mol) fatty acid B was esterified with 883.5 g (6.05 mol) bis-(2-hydroxypropyl)-methylamine with 4 h reaction at reduced pressure until the acid value of the reaction mixture was 3.3 mg KOH/g. Then 157 g refined coconut oil were added and the resulting mixture was reacted with 724.2 g (5.75 mol) dimethyl sulphate for 1 h. Thereafter, 472 g 2-propanol were added and the mixture was homogenized by stirring. The resulting fabric softener active composition was a white solid with a melting point of 36° C., containing 0.049 mmol/g (1.4% by weight) fatty acid and 0.125 mmol/g non-quaternised amine (0.067 mmol/g free amine and 0.058 mmol/g protonated amine). HPLC analysis showed the bis-(2-hydroxypropyl)-dimethylammonium methylsulphate fatty acid ester to be comprised of 6.3% monoester and 93.7% diester (rel. area percentages).

The composition had a melt viscosity of 144 mPa*s at 1 $s^{-1}$, 107 mPa*s at 10 $s^{-1}$ and 94 mPa*s at 100 $s^{-1}$ shear rate.

The composition achieved a softness rating of 34.

Example 16

Comparative Example, Corresponds to Example 50 of WO 00/06678

250 g (1.15 mol) Radiacid® 600 fatty acid was esterified with 176.3 g (1.21 mol) bis-(2-hydroxypropyl)-methylamine for 14 h at ambient pressure until the acid value of the reaction mixture was 2.6 mg KOH/g. The resulting mixture was reacted with 137.0 g (1.09 mol) dimethyl sulphate. The resulting fabric softener active composition was a yellow wax with a melting point of 35° C., containing 1.1% by weight fatty acid. HPLC analysis showed the bis-(2-hydroxypropyl)-dimethylammonium methylsulphate fatty acid ester to be comprised of 84.7% monoester and 15.3% diester (rel. area percentages).

The composition achieved a softness rating of 13.

Example 17

Comparative, Lower Molar Ratio of Fatty Acid Moieties to Amine Moieties 378.6 g (1.38 mol) fatty acid B was esterified with 211.5 g (1.45 mol) bis-(2-hydroxypropyl)-methylamine for 12 h at ambient pressure until the acid value of the reaction mixture was 3.8 mg KOH/g. The resulting mixture was reacted with 164.5 g (1.60 mol) dimethyl sulphate. The resulting fabric softener active composition was a yellow wax with a melting point of 40° C., containing 1.7% by weight fatty acid. HPLC analysis showed the bis-(2-hydroxypropyl)-dimethylammonium methylsulphate fatty acid ester to be comprised of 80.7% monoester and 19.3% diester (rel. area percentages).

The composition achieved a softness rating of 13.

Example 18

411.0 g (1.50 mol) fatty acid B was esterified with 146.0 g (1.0 mol) bis-(2-hydroxypropyl)-methylamine for 16 h at ambient pressure until the acid value of the reaction mixture was 5.0 mg KOH/g. The resulting mixture was reacted with 113.5 g (0.9 mol) dimethyl sulphate. The resulting fabric softener active composition was a yellow wax with a melting point of 38° C., containing 2.2% by weight fatty acid. HPLC analysis showed the bis-(2-hydroxypropyl)-dimethylammonium methylsulphate fatty acid ester to be comprised of 39.0% monoester and 61.0% diester (rel. area percentages).

The composition achieved a softness rating of 25.

Comparative examples 16 and 17 and example 18 demonstrate that a minimum molar ratio of fatty acid moieties to amine moieties of 1.5 is necessary to achieve a useful softening performance.

Example 19

Comparative, Quaternary Ammonium Chloride Salt 2780 g (10.18 mol) fatty acid B was esterified with 783 g (5.36 mol) bis-(2-hydroxypropyl)-methylamine with 3 h reaction at reduced pressure until the acid value of the reaction mixture was 5.2 mg KOH/g. 469.2 g of the resulting mixture were charged to a stirred autoclave, 195 g acetonirile was added and the autoclave was closed and heated to 75° C. 41.75 g (0.827 mol) methyl chloride were fed to the autoclave while stirring at 75° C. at a rate to keep the pressure in the reactor below 4 bar and the mixture was stirred for a total of 90 h at 75 to 80° C. Thereafter, pressure was released and unreacted methyl chloride and acetonirile solvent were distilled off. The resulting fabric softener active composition was a white solid with a melting point of 69° C., containing 0.085 mmol/g (2.3% by weight) fatty acid and 0.152 mmol/g non-quaternised amine (0.103 mmol/g free amine and 0.049 mmol/g protonated amine). HPLC analysis showed the bis-(2-hydroxypropyl)-dimethylammonium methylsulphate fatty acid ester to be comprised of 1.0% monoester and 99.0% diester (rel. area percentages).

The 10% aqueous dispersion had an acid value of 1.2 mg KOH/g and a viscosity of 66 mPa*s before storage, but split into two phases during storage for 6 weeks at 50° C.

Comparative example 19 demonstrates that the composition must comprise a quaternary ammonium methylsulphate salt in order to have a low melting point and provide stable aqueous dispersions, whereas a quaternary ammonium chloride salt leads to a high melting point and insufficient stability of aqueous dispersions.

Table 2 summarizes properties of the fabric softener active compositions prepared in examples 1 to 15. The fatty acid to amine molar ratio in table 2 refers to the molar ratio in the bis-(2-hydroxypropyl)-dimethylammonium methylsulphate fatty acid ester as calculated form the HPLC analysis. The data for acid value rise and viscosity change upon storage relate to 10% by weight aqueous dispersions of the fabric softener active compositions that were stored for 6 weeks at 50° C.

TABLE 2

Properties of the fabric softener active compositions

| Example | Fatty acid amine molar ratio | Fatty acid in wt-% | Melting point in ° C. | Melt viscosity at $1\ s^{-1}$ in mPa*s | Melt viscosity at $100\ s^{-1}$ in mPa*s | Acid value rise upon storage in mg KOH/g | Viscosity change upon storage in mPa*s | Softness rating |
|---|---|---|---|---|---|---|---|---|
| 1 * | 1.92 | 0.5 | <20 | 685 | 431 | 0.6 | 231 | 12 |
| 2 | 1.91 | 0.7 | 42 | 47200 | 2960 | 0.6 | 0 | 32 |
| 3 * | n.d. | 1.0 | ** | 561 | 469 | 0.7 | 110 | 24 |
| 4 | 1.97 | 0.9 | 43 | 36200 | 2160 | 0.7 | 2 | 31 |
| 5 | 1.95 | 2.2 | 41 | 2360 | 619 | 2.0 | −16 | 35 |
| 6 | 1.94 | 0.7 | 43 | 16200 | 1530 | 1.4 | −6 | 32 |
| 7 | 1.94 | 4.15 | 41 | 842 | 619 | 2.6 | −15 | 31 |
| 8 * | 1.93 | 1.6 | <20 | 581 | 480 | 1.7 | −4 | 23 |
| 9 * | 1.97 | 1.1 | ** | 552 | 497 | 1.7 | 49 | 16 |
| 10 | 1.83 | 1.3 | 41 | 27100 | 1870 | 1.6 | −6 | 27 |
| 11 | 1.99 | 2.2 | 43 | 1510 | 553 | 2.4 | −19 | 31 |
| 12 | 1.94 | 2.0 | 38 | 592 | 552 | n.d. | n.d. | n.d. |
| 13 | 1.93 | 1.9 | 52 | 34700 | 2630 | n.d. | n.d. | n.d. |
| 14 | 1.93 | 2.4 | 40 | 368 | 318 | n.d. | n.d. | n.d. |
| 15 | 1.94 | 1.4 | 36 | 144 | 94 | n.d. | n.d. | n.d. |

* not according to the invention;
** gel;
n.d. = not determined

What is claimed is:

1. A fabric softener active composition, comprising:
   a) at least 50% by weight of a bis-(2-hydroxypropyl)-dimethylammonium methylsulphate fatty acid ester, having:
      i) a molar ratio of fatty acid moieties to amine moieties of from 1.5 to 1.99;
      ii) an average chain length of the fatty acid moieties of from 16 to 18 carbon atoms; and
      iii) an iodine value of the fatty acid moieties, calculated for the free fatty acid, of from 0.5 to 50, and
   b) from 0.5 to 5% by weight fatty acid.

2. The fabric softener active composition of claim 1, wherein the molar ratio of fatty acid moieties to amine moieties is from 1.85 to 1.99.

3. The fabric softener active composition of claim 1, wherein the iodine value of the fatty acid moieties, calculated for the free fatty acid, is from 5 to 40.

4. The fabric softener active composition of claim 1, wherein the iodine value of the fatty acid moieties, calculated for the free fatty acid, is from 15 to 35.

5. The fabric softener active composition of claim 1, comprising from 1 to 5% by weight fatty acid.

6. The fabric softener active composition of claim 1, comprising from 2 to 5% by weight fatty acid.

7. The fabric softener active composition of claim 1, wherein said composition comprises from 85 to 99% by weight of bis-(2-hydroxypropyl)-dimethylammonium methylsulphate fatty acid ester.

8. The fabric softener active composition of claim 1, wherein the bis-(2-hydroxypropyl)-dimethylammonium methylsulphate fatty acid ester comprises less than 6% by weight of multiply unsaturated fatty acid moieties.

9. The fabric softener active composition of claim 1, wherein the cis-trans ratio of double bonds of the unsaturated fatty acid moieties of the bis-(2-hydroxy-propyl)-dimethylammonium methylsulphate fatty acid ester is higher than 55:45.

10. The fabric softener active composition of claim 1, wherein the fatty acid moieties of the bis-(2-hydroxypropyl)-dimethylammonium methylsulphate fatty acid ester are derived from the fatty acid of component b).

11. The fabric softener active composition of claim 1, wherein said composition comprises less than 2% by weight of water.

12. The fabric softener active composition of claim 1, wherein said composition comprises less than 0.5% by weight of water.

13. The fabric softener active composition of claim 1, wherein said composition comprises less than 10% by weight of solvents having a flash point of less than 20° C.

14. The fabric softener active composition of claim 1, wherein said composition comprises less than 1% by weight of solvents having a flash point of less than 20° C.

15. The fabric softener active composition of claim 1, further comprising up to 9.9% by weight of at least one solvent selected from glycerol, ethylene glycol, propylene glycol, dipropylene glycol and C1-C4 alkyl monoethers of ethylene glycol, propylene glycol and dipropylene glycol.

16. The fabric softener active composition of claim 1, further comprising from 2 to 8% by weight of a fatty acid triglyceride having an average chain length of fatty acid moieties of from 10 to 14 carbon atoms and an iodine value, calculated for the free fatty acid, of from 0 to 15.

17. The fabric softener active composition of claim 1, further comprising from 1.5 to 9% by weight of a bis-(2-hydroxypropyl)-methylamine fatty acid ester containing the same fatty acid moieties as the bis-(2-hydroxypropyl)-dimethylammonium methylsulphate fatty acid ester.

18. A method for making the fabric softener active composition of claim 1, comprising the steps of:
   a) reacting bis-(2-hydroxypropyl)-methylamine with a fatty acid having an average chain length of from 16 to 18 carbon atoms and an iodine value of from 0.5 to 50 in a molar ratio of fatty acid to amine of from 1.51 to 2.1 with removal of water until the acid value of the reaction mixture is in the range from 1 to 10 mg KOH/g; and
   b) reacting the product of step a) with dimethyl sulphate at a molar ratio of dimethyl sulphate to amine of from 0.90 to 0.97 until the total amine value of the reaction mixture is in the range from 1 to 8 mg KOH/g.

19. The method of claim 18, wherein the product of step a) is reacted with dimethyl sulphate at a molar ratio of dimethyl sulphate to amine of from 0.92 to 0.95 until the total amine value of the reaction mixture is in the range from 1 to 8 mg KOH/g.

20. The method of claim 18, wherein the molar ratio of fatty acid to amine is from 1.86 to 2.1.

* * * * *